United States Patent [19]

Falk

[11] 4,069,715
[45] Jan. 24, 1978

[54] MOLTEN METAL SAMPLER WITH OFFSET CONNECTOR

[76] Inventor: Richard A. Falk, 519 Westminster Drive, Waukesha, Wis. 53186

[21] Appl. No.: 744,481

[22] Filed: Nov. 24, 1976

[51] Int. Cl.² ............................................. G01N 1/12
[52] U.S. Cl. .................................. 73/354; 73/425.4 R
[58] Field of Search .................... 73/425.4 R, DIG. 9, 73/354

[56] References Cited

U.S. PATENT DOCUMENTS

| | | | |
|---|---|---|---|
| 3,357,250 | 12/1967 | Lowdermilk | 73/DIG. 9 |
| 3,503,259 | 3/1970 | Carlson et al. | 73/DIG. 9 |

*Primary Examiner*—S. Clement Swisher
*Attorney, Agent, or Firm*—Henry C. Fuller

[57] ABSTRACT

Molten metal sampling apparatus includes two or more paperboard sleeves held together in side by side relationship by glue, fasteners and a refractory cement joint with one of the sleeves being connectible by a friction-fit to a handle inserted in one of the sleeves and the other of the sleeves containing a sample mold. The handle is a paperboard tube which carries a thermocouple for measuring bath temperature. Additional sleeves can be added to carry sample molds of a different configuration. The sampling apparatus is adaptable for handling a wide range of sample molds and is inexpensive and relatively compact and enables taking of a sample and a bath temperature simultaneously.

5 Claims, 4 Drawing Figures

U.S. Patent
Jan. 24, 1978
4,069,715
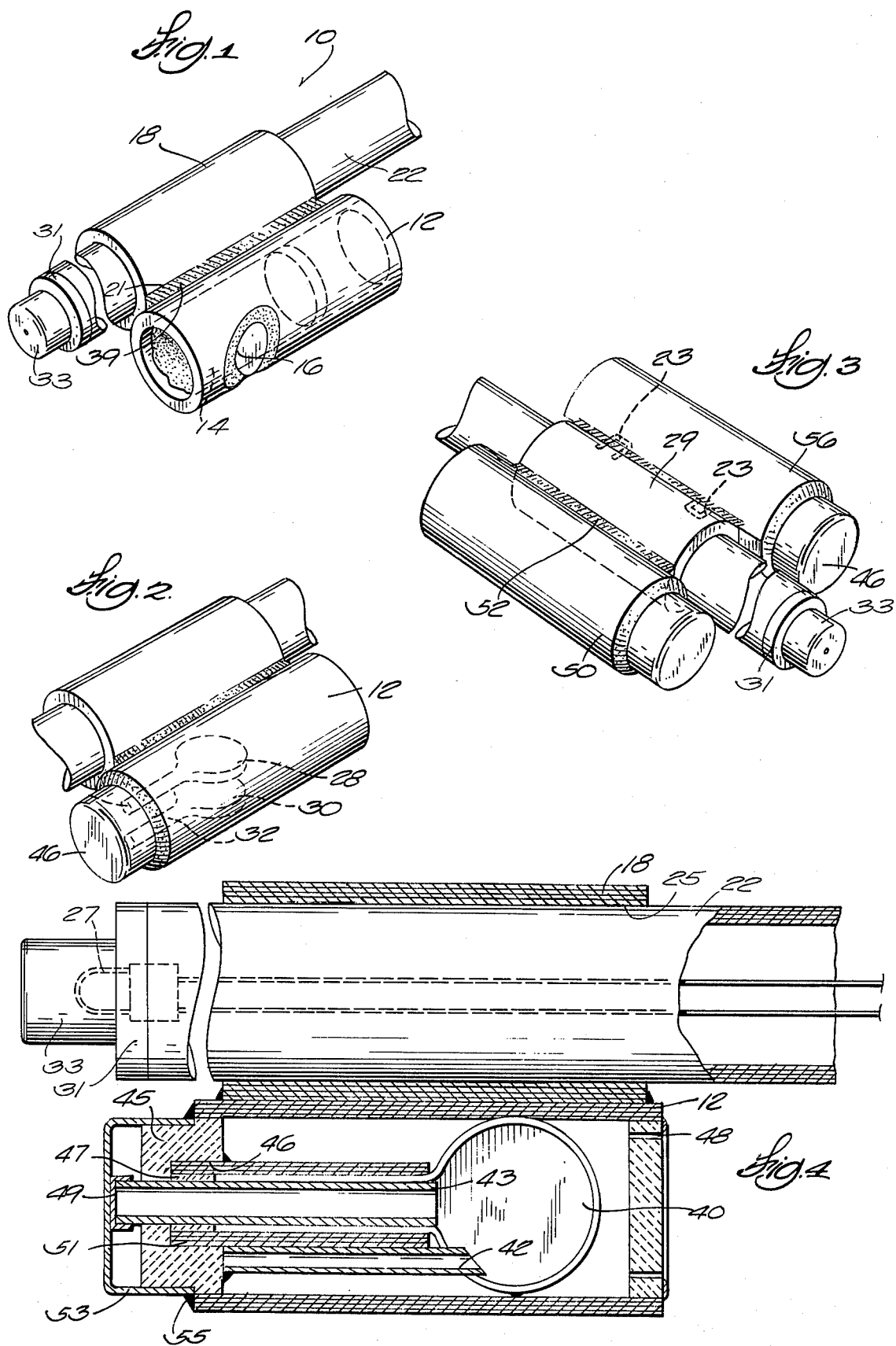

MOLTEN METAL SAMPLER WITH OFFSET CONNECTOR

SUMMARY OF INVENTION

The invention provides a piggyback arrangement for combining molten metal sampling devices in which any one of various types of sample molds can be carried in one or more short paperboard sleeves. An open ended paperboard sleeve is joined to a sleeve carrying a sample mold by glue, and/or fasteners and a refractory cement joint which provides an extremely rigid connection. A handle in the form of a paperboard sleeve carrying a thermocouple is inserted through the open ended sleeve.

The sampling apparatus of the invention enables use of a common handle to manipulate various molten metal analyzing equipment which can include two or more sample molds and thermocouples for measuring bath temperature and phase change temperatures to determine carbon content.

Further objects, advantages and features of the invention will be apparent from the disclosure.

DESCRIPTION OF DRAWINGS

FIG. 1 is a perspective view of immersion sampling apparatus in accordance with the invention with a sample mold having a side entry port.

FIG. 2 is a perspective view similar to FIG. 1 showing two sample molds constructed of split mold halves.

FIG. 3 is a perspective view with a thermocouple in one sleeve and a sample mold in another sleeve.

FIG. 4 is an enlarged fragmentary sectional view of one form of sample mold.

DESCRIPTION OF PREFERRED EMBODIMENT

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

In the drawings FIG. 1 shows molten metal sampling apparatus 10 which includes a paperboard sleeve 12 which contains a refractory cartridge 14 with a side entry port 16 and a cylindrical interior. The refractory cartridge 14 can be constructed as described in my U.S. Pat. No. 3,481,201. Means are provided to secure the sleeve 12 to a mounting sleeve 18. In the construction disclosed in FIG. 1 the sleeves 18, 12 are glued together by fast drying glue 21 such as white glue along the linear contact line of the two sleeves 18, 12. The joint is filled in with refractory cement 39 which can extend the full length of the sleeves 12 and 18. The refractory cement joint rigidly secures the two sleeves 12 and 18 together and protects the glue bond. In FIG. 3 each of the outer sleeves is provided with a flat 19 and the inner sleeve 29 is provided with two flats 19 at 180°. The flats are parallel to a plane through the longitudinal axis of the sleeves and provide a good glue 21. The sleeves can also be stapled together by staples 23 to provide more strength in the joints which is particularly important during immersion of the samplers in molten metal. The staples or other fasteners can be inserted with small staple guns which are inserted in the sleeves.

The sampling apparatus 10 includes a paperboard handle 22 which is sized to frictionally interfit in the bore 25 of sleeve 18. The paperboard handle 22 must tightly fit into the bore 25 to prevent metal flow into the bore during immersion. Any metal flow can cause loss of the sample cartridge in the melt. Pins or fasteners can be employed to secure the handle 22 in the sleeve 18. The handle 22 carries a thermocouple element 27 (FIG. 4) which is protected by a fusible cap 33. The thermocouple element is connected to a recording apparatus by wires (not shown). The end 31 of the handle 22 is located at a substantial distance such as 5–8 inches from the sleeve 12 when the handle is inserted in the sleeve 18 to prevent interference with the measurement of bath temperature caused by boiling and combustion of tube 12. The handle 22 enables manipulation of the sample mold in a metal bath as well as the taking of bath temperature.

FIG. 2 shows another immersion sampler in which the sleeve 12 contains two sample molds 28 and 30 each of which are provided with a fill tube 32. The sample molds 28, 30 can each be constructed of two mold halves as disclosed in my U.S. Pat. No. 3,805,621.

FIG. 4 shows a sampler with a sample mold 40 having a pin sample tube 42 similar to that shown in my U.S. Pat. No. 3,791,219. The sample mold 40 has a fill tube 43 which extends beyond the end 44 of the sleeve 12 and through a refractory annulus 45 which protects the fill tube which is normally fused quartz. The annulus 45 has a recess 46 which receives a paperboard sleeve 51 which is cemented in the annulus by cement 47 to integrate the annulus and sample mold. The annulus is sized to provide a friction fit in the sleeve 12. A bead 55 of refractory cement secures the sample cartridge in the sleeve 12. The fill tube 43 can be provided with a cap 49 formed of a deoxidant. A fusible protective cap 53 protects the fill tube 43. The interior of the sleeve 12 is vented through vents 48.

The embodiment shown in FIG. 3 includes a sleeve 50 which can be provided with a thermocouple 54 for measuring phase change temperature to determine carbon content or a different type of sample cartridge than that contained in the sleeve 56. More than three sleeves can be employed to form a cluster of sampling equipment manipulated by one handle.

The use of a pair or cluster of short paperboard sleeves with one sleeve serving as a coupling with a handle and other sleeves as a carrier for sampling equipment enables convenient and simultaneous retrieval of multiple samples taken from substantially the same position in the melt. Three or four equipment sleeves can be conveniently carried by a handle connecting sleeve.

I claim:

1. Molten metal sampling apparatus comprising a first paperboard sleeve, a sample mold in said first sleeve, means defining a fill passage for delivery of molten metal to said sample mold, a second paperboard sleeve, fastening means for securing said first and second sleeves in side by side relationship, a handle, and means for detachably connecting said handle to said second sleeve.

2. Molten metal sampler in accordance with claim 1 wherein said handle includes a thermocouple for measuring the temperature of the metal bath.

3. Sampling apparatus in accordance with claim 1 wherein said sleeves have longitudinally extending flats in abutting contact, with glue on the flats.

4. Sampling apparatus in accordance with claim 1 wherein the fastening means includes fasteners extending through abutting sleeve surfaces.

5. Sampling apparatus in accordance with claim 1 wherein said handle comprises a third paperboard sleeve sized to frictionally interfit into said second sleeve and said third sleeve carrying a thermocouple for measuring bath temperature.

* * * * *